US00PP30794P2

(12) United States Plant Patent
Winslow

(10) Patent No.: US PP30,794 P2
(45) Date of Patent: Aug. 13, 2019

(54) ***IPOMOEA* PLANT NAMED 'BALSPOTIMART'**

(50) Latin Name: *Ipomoea batatas*
Varietal Denomination: Balspotimart

(71) Applicant: Ball Horticultural Company, West Chicago, IL (US)

(72) Inventor: Benjamin K. Winslow, Austin, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/932,581

(22) Filed: Mar. 16, 2018

(51) Int. Cl.
*A01H 5/02* (2018.01)
*A01H 6/00* (2018.01)

(52) U.S. Cl.
USPC ..... Plt./258

(58) Field of Classification Search
USPC ..... Plt./258, 263.1, 226
CPC ... A01H 5/12; A01H 5/06; A01H 5/02; A01H 5/04; A01H 5/00; A01H 6/00
See application file for complete search history.

(56) References Cited

PUBLICATIONS

Ball Seed Spotlight Lime Heart *Ipomoea*, retrieved on Feb. 28, 2019, retrieved from the Internet at https://www.ballseed.com/PlantInfo/?phid=060201785039700, one page. (Year: 2019).*

UGA Trial Gardens 2018 Trial Results *Ipomoea* 'Spotlight Lime Heart', retrieved on Feb. 28, 2019, retrieved from the Internet at http://ugatrial.hort.uga.edu/index.cfm?fuseaction=plants.plantDetail&plant_id=23853, one page. (Year: 2018).*

* cited by examiner

*Primary Examiner* — June Hwu
(74) *Attorney, Agent, or Firm* — Audrey Charles

(57) ABSTRACT

A new and distinct cultivar of an ornamental *Ipomoea* plant named 'Balspotimart', characterized by shallowly-lobed, medium lime-green colored foliage, and moderately vigorous, compact, mounded-spreading growth habit, is disclosed.

1 Drawing Sheet

Latin name of genus and species of plant claimed: *Ipomoea batatas*.

Variety denomination: 'Balspotimart'.

BACKGROUND OF THE INVENTION

The present invention relates to a new and distinct cultivar of *Ipomoea* plant botanically known as *Ipomoea batatas* and hereinafter referred to by the cultivar name 'Balspotimart'.

The new cultivar originated in a controlled breeding program in Arroyo Grande, Calif. during October 2013. The objective of the breeding program was the development of ornamental *Ipomoea* cultivars with heart-shaped leaves, and a well-branched, mounded growth habit with good garden performance under high night temperatures.

The new ornamental *Ipomoea* cultivar is the result of cross-pollination. The female (seed) parent of the new cultivar is the proprietary breeding selection BW028-023, unpatented, characterized by its medium lime-green colored foliage and moderately vigorous, compact, mounded-spreading growth habit. The male (pollen) parent of the new cultivar is the proprietary breeding selection B W009-013, unpatented, characterized by its medium lime-green colored foliage and moderately vigorous, compact, mounded-spreading growth habit. The new cultivar was discovered and selected as a single plant within the progeny of the above stated cross-pollination during April 2014 in a controlled environment in Arroyo Grande, Calif.

Asexual reproduction of the new cultivar by terminal stem cuttings since April 2014 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspotimart' as a new and distinct cultivar of *Ipomoea* plant:

1. Shallowly-lobed, medium lime-green colored foliage; and
2. Moderately vigorous, compact, mounded-spreading growth habit.

Plants of the new cultivar differ from plants of the female and male parents primarily in maintaining plant habit and foliage color under high sunlight conditions and high night temperatures. In addition plants of the new cultivar differ from plants of the male parent in having more shallowly-lobed foliage.

Of the many commercially available ornamental *Ipomoea* cultivars, the most similar in comparison to the new cultivar is Spotlight Lime, 'Balspotime', U.S. Plant Pat. No. 28,588. However, in comparison, plants of the new cultivar differ from plants of 'Balspotime' in at least the following characteristics:

1. Plants of the new cultivar have more shallowly-lobed foilage than plants of 'Blaspotime';

2. Plants of the new cultivar do not have branches with a greyed-purple overlay when developing like plants of 'Balspotime'; and
3. Plants of the new cultivar have smaller leaves than plants of 'Balspotime'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balspotimart'. The plants were grown in one-gallon pots for 11 weeks in a greenhouse in Arroyo Grande, Calif.

DETAILED BOTANICAL DESCRIPTION

Figure 1:
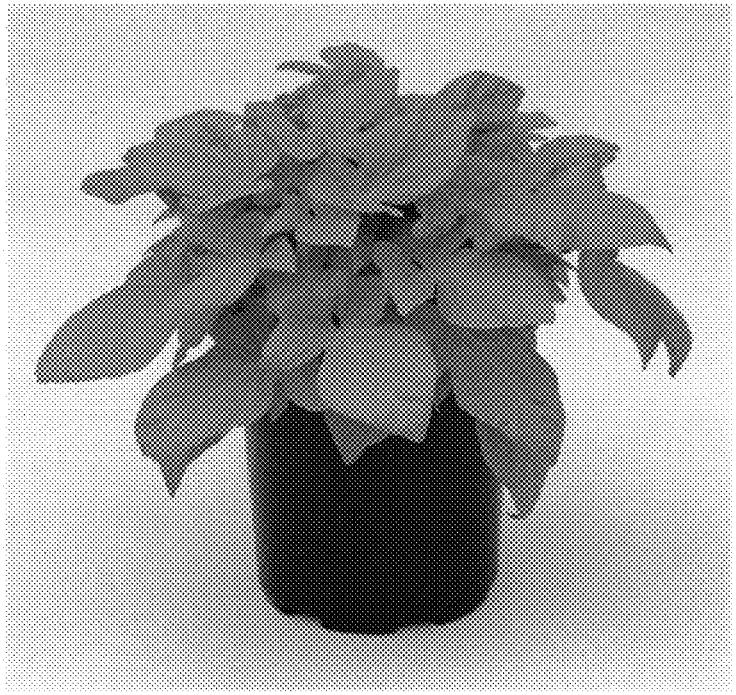
FIG. 1 illustrates a side view of the overall growth and habit of 'Balspotimart'.
Figure 2:
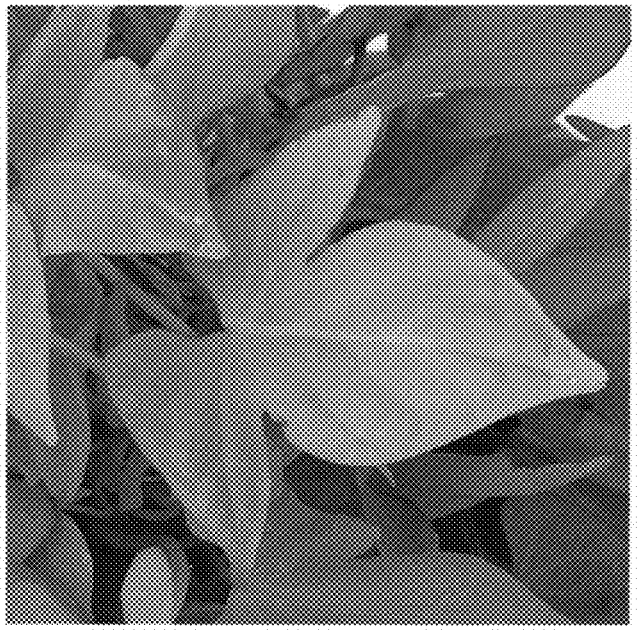
FIG. 2 illustrates a close-up view of an individual leaf of 'Balspotimart'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2018 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 10 weeks in a greenhouse utilizing a soilless growth medium. Greenhouse temperatures were maintained at approximately 68° F. to 72° F. (20° C. to 22° C.) during the day and approximately 64° F. to 66° F. (18° C. to 19° C.) during the night. Supplemental lighting was used. Measurements and numerical values represent averages of typical plants.

Botanical classification: *Ipomoea batatas* 'Balspotimart'.

Parentage:

*Female parent.*—Proprietary breeding selection BW028-023, unpatented.

*Male parent.*—Proprietary breeding selection BW009-013, unpatented.

Propagation:

*Type cutting.*—Terminal stem.

*Time to initiate roots.*—Approximately 3 to 4 days.

*Time to produce a rooted cutting.*—Approximately 21 to 28 days.

*Root description.*—Fibrous, medium thickness, white to light brown in color.

*Rooting habit.*—Freely branching.

*Tuber description.*—Not available, tuber formation not observed to date.

Plant description:

*Commercial crop time.*—Approximately 4 to 5 weeks from a rooted cutting to finish in a 10 cm pot.

*Growth habit and general appearance.*—Moderately vigorous, compact, mounded-spreading growth habit.

*Size.*—Height: Approximately 8.0 cm. Width: Approximately 22.0 cm.

*Branching habit.*—Freely branching, pinching enhances basal branching. Quantity of main lateral branches per plant: Approximately 3, axils have latent shoots.

*Branch.*—Shape: Round. Strength: Strong, slightly flexible. Length: Approximately 4.0 cm. Diameter: Approximately 5.0 mm. Length of central internode: Approximately 3.0 mm. Texture: Densely pubescent. Color of young and mature stems: 145B.

Foliage description:

*General description.*—Quantity of leaves per branch: Approximately 8. Fragrance: None detected. Form: Simple. Arrangement: Alternate, spiral.

*Leaves.*—Shape: Roughly cordate in overall form, shallowly 3-lobed, lobes deepen in depth when plants are grown and under long-day conditions and high light intensity. Margin: Entire. Apex of central lobe: Broadly acuminate. Apex of lateral lobes: Broadly acute. Base: Cordate. Venation pattern: Palmate with arcuate venation in the center lamina. Length of mature leaf: Approximately 7.5 cm. Width of mature leaf: Approximately 5.5 cm. Length of central lobe: Approximately 4.5 cm. Width of central lobe: Approximately 3.5 cm. Texture of upper and lower surfaces: Glabrous. Color of upper surface of young foliage: N144D with slightly lighter colored venation. Margins and an overlay of 187A when plants are grown under long-day conditions and high light intensity. Color of lower surface of young foliage: Closest to 145B with venation of 145C. Color of upper surface of mature foliage: N144D to 145A with slightly lighter colored venation. Color of lower surface of mature foliage: Closest to 147D with venation of 145C.

*Petiole.*—Length: Approximately 5.5 cm. Diameter: Approximately 3.0 mm. Texture: Glabrous. Color: 145B.

Flowering description: Not available, flower and seed formation not observed to date. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balspotimart', substantially as herein illustrated and described.

* * * * *